Figure 1:
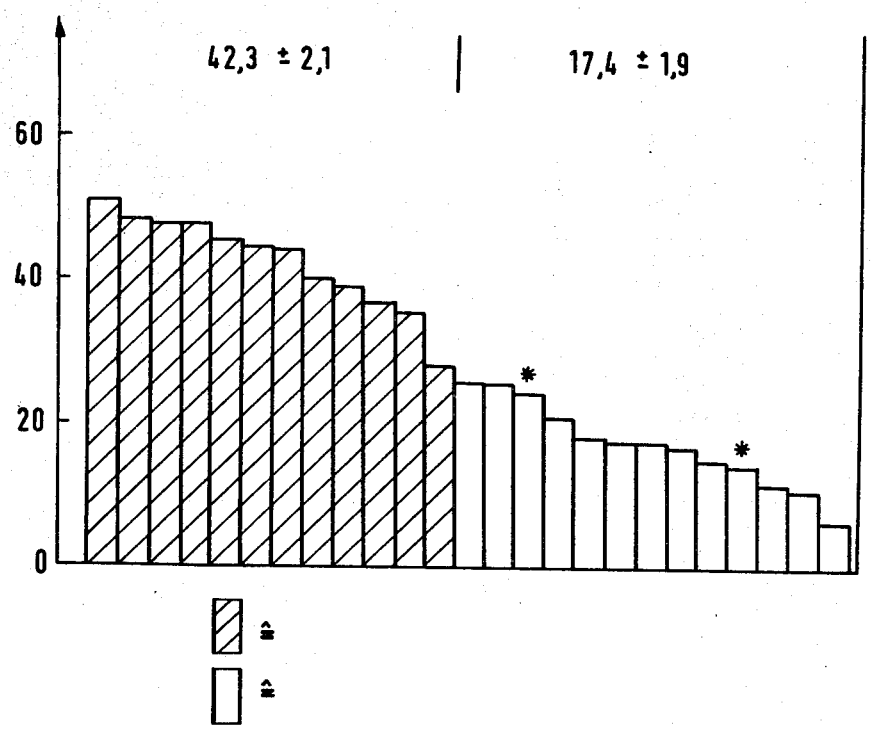

United States Patent [19]

Bürk et al.

[11] 4,403,041

[45] Sep. 6, 1983

[54] DIAGNOSIS OF ATHEROSCLEROSIS

[75] Inventors: Robert R. Bürk, Bottmingen; Peter Clopath, Basel; Klaus Müller, Ettingen, all of Switzerland

[73] Assignee: Ciba-Geigy Corporation, Ardsley, N.Y.

[21] Appl. No.: 128,744

[22] Filed: Mar. 10, 1980

[30] Foreign Application Priority Data

Mar. 15, 1979 [CH] Switzerland ................. 2454/79

[51] Int. Cl.³ ............... G01N 13/00; G01N 33/48; C12N 5/00; C12N 5/02
[52] U.S. Cl. ............................ 436/501; 436/503; 436/506; 436/514; 436/515; 436/519; 435/240; 435/241
[58] Field of Search ............... 424/1, 8, 12; 23/230 B; 436/501, 503, 506, 514, 515, 519; 435/240, 241

[56] References Cited

U.S. PATENT DOCUMENTS

| | | | |
|---|---|---|---|
| 4,059,486 | 11/1977 | Tolbert | 435/1 |
| 4,081,241 | 3/1978 | Porzsolt | 436/519 |
| 4,299,814 | 10/1981 | Brandt | 436/519 |

FOREIGN PATENT DOCUMENTS 2370094 6/1978 France .

OTHER PUBLICATIONS

Lab, Invest., vol. 36, 1974, pp. 18-25.
Burk, Proc. Nat. Acad. Sci., USA, vol. 70, 1973, pp. 369-372.
Selivanov, Sov. Med., Jan. 1979, (1), pp. 35-40.
De Bono, Nature, vol. 252, 1974, pp. 83-84.
Biochem. Soc. Trans., vol. 5, 1977, pp. 1181-1183.
Porter, J. Cell. Biol., vol. 59, 1973, pp. 633-642.
Sholley, Lab. Invt., vol. 36, 1977, pp. 18-25.
Burk, Artery, vol. 6(3), 1979, pp. 205-219.

Primary Examiner—Anna P. Fagelson
Attorney, Agent, or Firm—Irving N. Feit

[57] ABSTRACT

A novel method of diagnosis of atherosclerosis comprises comparing the migration of endothelial cells or of cells of endothelium-like morphology in vitro, in the presence of serum from the person being examined, with the migration of identical cells in the presence of serum from healthy persons or of other standard sera, and interpreting a reduced migration in the presence of serum of the person being examined as being an indication of the possible existance of atherosclerosis in this person. The cell migration is measured for example on monolayer cell cultures of pig aorta endothelial cells or of Balb/c 3T3-A31 cells, in which cultures a portion of the cellular layer has been removed. An outfit for carrying out the method contains the materials and devices necessary for the purpose.

11 Claims, 3 Drawing Figures

DIAGNOSIS OF ATHEROSCLEROSIS

The present invention relates to a method of diagnosis, particularly to a method for the diagnosis of arterosclerosis, and to an outfit for carrying it out.

It has been acccepted for a considerable time that atherosclerosis commences with an injury to the arterial endothelium. As a result of injury in the endothelium, the subendothelial connective tissue becomes exposed to the influences of components of the circulating blood. Blood platelets adhere to the exposed surface of the connective tissue, aggragate, and release, besides other substances, a growth factor which, as was possible to verify, stimulates the proliferation of smooth muscle cells in vitro. Under normal conditions, there occurs endothelial regeneration by virtue of a combination of migration and proliferation of cells, and within a few days the blood consequently becomes sealed off from the subendothelial tissue. The cumulative effect of short phases of proliferation of smooth muscle cells is observed as a modest thickening of the vascular intima with advancing age. It is assumed that atherosclerotic lesions, that is to say, focal excessive intimal thickening, develop at sites of repeated endothelial injury. Advanced vascular lesions contain an excessive amount of the lipids in the core covered by a fibrous cap containing dense collagen and hyperplastic smooth muscle cells. According to various references, the formation of atherosclerotic lesions is accelerated also by high concentrations of serum lipids.

The method of diagnosis according to the invention is based on the establishment of the fact not hitherto known that the migration of endothelium cells, or of cells having endothelial properties, in vitro is less in the presence of serum of experimental animals, especially pigs, which have been kept on an atherogenic diet, and likewise in the presence of serum from atherosclerosis patients, than it is in the presence of serum from normally fed experimental animals or from healthy persons. A reduced migration in vivo could result in the replacement of lost cells and the sealing of small perforations in the endothelium being retarded, and hence promote the formation of atherosclerotic lesions. The reduced migration would therefore in no way be contrary to the known findings summarised above concerning the occurrence of atherosclerotic lesions.

The method according to the invention for the diagnosis of atherosclerosis comprises comparing the migration of endothelial cells or of cells of endothelium-like morphology in vitro, in the presence of serum from the person being examined, with the migration of identical cells in the presence of serum from healthy persons or of other standard sera; and interpreting a reduced migration in the presence of serum of the person being examined as being an indication of the possible existence of atherosclerosis in this person. Endothelial cells usable for the method according to the invention are for example those from the pig aorta [cp. D. De Bono, Nature 252, 83–84 (1974) and J. D. Pearson et al., Biochem. Soc. Transactions 5, 1181–1183 (1977)]; and other cells having endothelium-like morphology are in particular Balb/c 3T3-A31 cells, a mouse cell strain to which are attributed endothelial properties [cp. K. R. Porter, G. J. Todaro and V. A. Fonte J. Cell. Biol. 59, 633–642 (1973)]. Of importance is in any case that the employed endothelium-like cells form a monolayer cell culture.

The measurement of cell migration is carried out preferably on monolayer cell cultures, in which a portion of the cellular layer is removed, that is to say, one or more wounds have been induced. In order to establish the involvement both of replication and migration in the restoration of damaged endothelium by in vitro tests, M. M. Sholley, M. A. Gimbrone and R. S. Cotran, [Laboratory Investigation 36, 18–25 (1977)] measured the degree of repopulation of scratches, 0.4–0.5 mm in width, made in monolayers of endothelial cells of human umbilical veins; and in addition to ascertaining the cell density, they also measured the extent of DNA synthesis on the basis of the intake of $^3$H-thymidine, and to determine the migration component, replication was eliminated by irradiation in the case of a number of specimens, a measure which simultaneously quite considerably reduced the intake of $^3$H-thymidine. Much more suitable and simple for the quantitative assessment of migration alone is however a procedure described by R. R. Bürk [in Proc. Nat. Acad. Sci. U.S.A. 70, 369–372 (1973)] for a different objective, namely the measurement of the stimulation of the migration of Balb/c 3T3 cells by a migration factor released by a tumorous cell line SV 28 in a serum-free medium, the behaviour of these Balb/c 3T3 cells being then compared with that of normal Balb/c 3T3 cells in the absence and in the presence of serum.

Employing this procedure, monolayer cultures of Balb/c 3T3-A31 cells are grown in plastic Petri dishes, in a manner which is slightly modified and which is described in more detail in the following Example 1, using a suitable nutrient solution, such as Dulbecco's Medium (Gibco H21 HG) containing 10% of fetal calf serum (Gibco), as well as penicillin and streptomycin; and subsequently there is applied, with a rigid razor-blade or half of a razor-blade, depending on the size of the dish, a wound about 1 cm wide, which is sharply defined on one side and which extends into the plastic bottom of the dish. Measurements are then made, with the addition of fresh medium containing for example 4% or 8% of the patient's serum and of the normal serum serving as a comparison, respectively, of the migration occurring. The applying of a wound of the given size and in the described manner is also very advantageous where other monolayer cell cultures are used.

As a measure of migration, there is taken for example the number of cells which have migrated, per millimeter of the sharp boundary line, over this line into the initially cell-free wound. This number is designated in the Examples as 'migration unit'. Because cell division commences after 30 hours, the duration of the test is limited to less than 30 hours, for example to 22 hours, so that measures to prevent replication are unnecessary. Instead of using Balb/c 3T3-A31, cells, it is also possible to use for example endothelial cells from the pig aorta.

In order that the significance of the reduced migration activity of patient's serum on a specific monlayer cell culture can be better assessed, it is advantageous to concomitantly determine, on identically prepared monolayer cell cultures, not only the migration activity of normal serum but also that of serum having a known greatly reduced migration activity, that is to say, to use two standard sera in place of one. Instead of originating from selected persons or groups of persons, standard sera of this type can come for example from specially fed pigs, that is, from pigs fed on either a nonatherogenic diet or an atherogenic diet. It is however clear that also in this case the migration activity of sera from normal persons remains the pertinent comparative criterion with which the pig sera are compared and standardized and then used as an equivalent of the human standard.

As shown particularly from the following Example 4, the method according to the invention is well suited for controlling the success of therapeutic and/or dietary measures in the case of existing or suspected atherosclerosis.

The Examples which follow are intended to further illustrate the invention.

EXAMPLE 1

Determination of migration units (number of migrated cells per millimeter of boundary line) of the sera from minipigs fed on an atherogenic diet and from normally fed minipigs.

(a) Experimental animals: There were used in all 25 minipigs for the tests. Normal pig feed was fed to 12 of these animals, whilst 11 pigs received an atherogenic diet containing, in addition to normal pig feed, lard, cholesterol and peanut oil, during 4 weeks before taking of serum; and 2 pigs received the same atherogenic diet during only 2 weeks before serum was taken.

(b) Method: Balb/c 3T3-A31 cells, in the following designated as 3T3-B cells, were maintained by further culturing in the ratio of 1 to 5 three times per week in each case before confluence, in Dulbecco's medium (Gibco H21 HG) having a content of penicillin and streptomycin as well as 10% of fetal calf serum (Gibco) which had been inactivated by being heated to 56° C. for 30 minutes. There were introduced $1 \times 10^5$ 3T3-B cells into 2.5 ml of medium in each plastic Petri dish of 35 mm diameter (for tissue culture). After 5 days' incubation at 37° C., a wound was made in each dish by lightly pressing half of a rigid razor blade (for example Personna Gem, reg. trademark) through the cellular layer into the plastics base to mark a boundary line, and moving the blade with lighter pressure perpendicular to this line to a distance of about 10 mm. The medium together with the scraped-off cells was then drawn off by suction. There were then introduced 2.4 ml of fresh medium consisting of Dulbecco's medium (Gibco H21 HG) with penicillin and streptomycin, followed by 100 $\mu$l of the serum to be tested, corresponding to 4%. After 22 hours, the medium was drawn off by suction, and the cellular layer was fixed and simultaneously dyed with the aid of Leishman's dye in methanol (1.5 g of dye per liter of methanol, 1.5 ml of solution per dish). After 10 minutes, 3.5 ml of water were added, and after a further 45 minutes, the dish was thoroughly rinsed with running water and dried. The evaluation consisted of counting for example the cells (nuclei) on 3 strips each 1.2 mm wide at right angles to the boundary line.

(c) Results: In FIG. 1 are summarised the results of migration determinations according to decreasing migration units (=number of cells per millimeter of boundary line, given on the axis of ordinates). Hatched bands signify migration units of the sera of normally fed pigs, and blank strips the migration values of the sera of pigs fed on an atherogenic diet, the values of the two pigs fed on an atherogenic diet for only 2 weeks being marked with an asterisk. When the sera are divided into two halves on the basis of their migration units, the sera of all normally fed pigs are in the half having higher migration values of $42.3 \pm 2.1$ on average, and all sera of the pigs fed on an atherogenic diet are in the half having lower migration values of $17.4 \pm 1.9$ on average.

EXAMPLE 2

Determination of migration units of sera of arterosclerosis patients and of normal patients.

(a) Origin of the tested human sera: Sera of 29 atherosclerosis patients treated as outpatients and of 10 normal persons were used. The sera were kept at $-18°$ C. until tested.

(b) Method: Identical to that described in Example 1.

Figure 2:
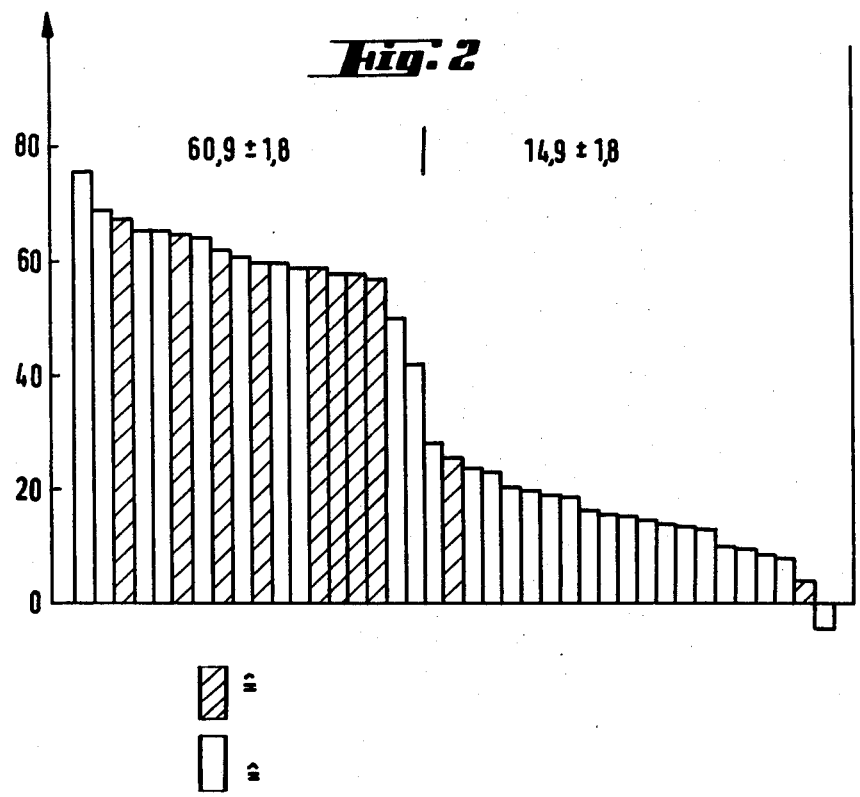

Results: The results of migration determinations are given in FIG. 2, again according to decreasing migration units (=number of cells per millimeter of boundary line, given on the axis of ordinates), with hatched bands for sera of normal persons and blank bands for sera of atherosclerosis patients. With division of the results into halves of higher and lower migration values, there are clearly shown more widely differing average values of $60.9 \pm 1.8$ and $14.9 \pm 1.8$ migration units, respectively. The sera of normal persons have migration values in the lower half; on the other hand the migration values of the sera of 8 atherosclerosis patients are not in the lower part or in the lower part of the upper half. The overall picture is therefore not quite so consistent as in Example 1; however, in the case of the sera of all together 19 of the 29 patients, the migration units ascertained were clearly lower than those of the whole of the normal persons; greatly reduced migration units are hence a characteristic symptom in about two thirds of the patients, whereas only in 2, that is, one fifth, of normal persons were approximately equally low migration units determined. Also remarkable is the clear separation of reduced and "normal" migration units, since only 2 of a total of 29 patients' sera gave values which could not be rated as belonging either to the "normal" half or to the half containing reduced values.

EXAMPLE 3

Comparison of the migration activity of human sera on 3T3-B cells (see Example 1) and on endothelial cells of pig aorta.

(a) Origin of the sera: The human sera used were two having high migration activity and three having low migration activity in the tests according to Example 2.

(b) Employed cell cultures: Pure cultures of pig aorta endothelial cells were prepared as follows: The endothelial cells were removed from the aortas of freshly slaughtered, 12-week old pigs with the aid of collagenase and with the minimum of mechanical operations [cp. J. D. Pearson et al., Biochem. Soc. Transactions 5, 1181–1183 (1977)], and were placed, together with Waymouth's medium 752/1, containing 20% of fetal calf serum, into Petri dishes. After confluence, $2 \times 10^5$ cells in each plastic Petri dish of 35 mm diameter containing 2.5 ml of Waymouth's medium, supplemented with 10% of fetal calf serum, were further cultivated, and after 5 days the cell cultures were used to determine migration activity (see c)).

The 3T3-B cell cultures used were those already described in Example 1.

(c) Method: Regarding the 3T3-B cell cultures, these were identical to those described in Example 1. In the case of the endothelial cell cultures from pig aorta, the method differed in the following points from the method of Example 1: The employed medium was Waymouth's 752/1. The cell density during the test was approximately twice as high as that in the dishes with 3T3-B cells, i.e. $10^5$ per $cm^2$ instead of about $5 \times 10^4$ per $cm^2$; the migration units given in the table relate therefrom likewise to an approximately twice as large cell number of the boundary line.

(d) Results: As can be seen from the following Table, the tested human sera, with regard to its migration activity, behaved on the endothelial cells from pig aorta essentially the same as on 3T3-B cells. The number of migrated pig aorta endothelial cells was in all cases lower than that of migrated 3T3-B cells; however, the differences in the migration activities of the various sera were even more pronounced, with a mean ratio of migration units of low-active to normally active human serum of 2.9 to 19.8, i.e. 1 to 6.8, compared with 14.8 to 58.2, i.e. 1 to 3.9, in the case of 3T3-B cells. From this it can be concluded that, for use in the method of diagnosis according to the invention, pig aorta endothelial cells are equally as suitable as the 3T3-B cells exclusively used in Examples 1 and 2.

TABLE for Example 3

| Serum No. | Migration units, determined on: | |
|---|---|---|
| | endothelial cells of pig aorta | 3T3-B cells |
| 9 | 1.6 | 14.9 |
| 12 | 3.2 | 15.2 |
| 13 | 3.8 | 14.3 |
| 29 | 18.0 | 57.6 |
| 34 | 21.6 | 58.7 |

EXAMPLE 4

Variation with time of migration activity of the sera of pigs on a changing diet.

(a) Experimental animals: there were used as such two female miniature pigs which at the commencement of the test were 4 months old and weighed 12 kg each.

(b) Mode of feeding: The animals received during the first 4 weeks normal pig feed, then during 4 weeks an atherogenic diet, i.e. pig feed with an addition of lard, cholesterol and peanut oil, and finally for 8 weeks again the normal pig feed.

(c) Determination of migration activity: Serum was taken once weekly and kept at $-18°$ C. until an evaluation was made. The migration activity of the sera was measured as number of migration units in a manner completely analogous to that of Example 1. Additionally determined in each case in the customary manner was the cholesterol level.

Figure 3:
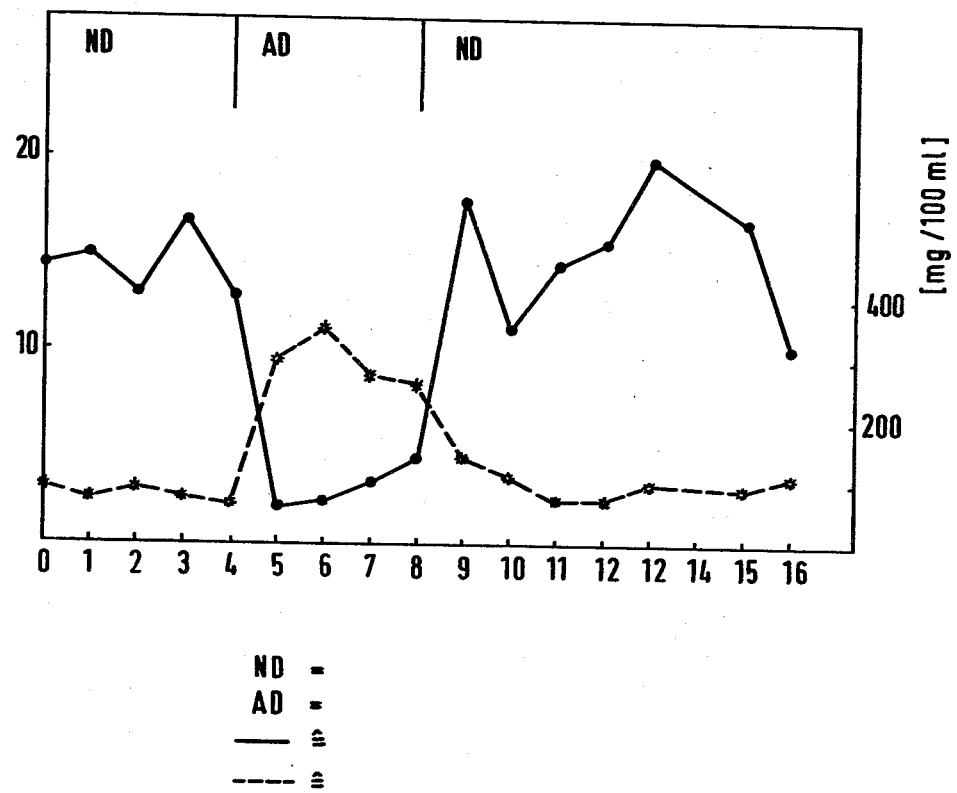

Results: The weekly determined (number of weeks given on the axis of abscissas) migration units as mean values of the sera of both pigs (number of cells per millimeter of boundary line, given on the lefthand axis of ordinates) and the respective cholesterol levels (in mg/100 ml, given on the righthand axis of ordinates) are summarised in FIG. 3. The corresponding curves show definitely that, after the changeover from normal diet (ND) to atherogenic diet (AD), the migration activity (full lines) falls at least as rapidly as the cholesterol level (in mg/100 ml, broken lines) increases, and that after the return to normal feeding the orignal values are again attained, although somewhat less rapidly.

A further subject matter of the present invention is an outfit for carrying out the method of diagnosis according to the invention, which outfit contains the required materials and devices mentioned in the specification and in the Examples: namely suitable cells for monolayer cell culture, for example selected from the Balb/c 3T3-A31 line, or selected endothelial cells from arteries of pigs or cattle, or selected endothelial cells from human umbilical veins;

animal serum, suitable for preparing the monolayer cell culture, for example a selected and tested fetal calf serum or horse serum;

a suitable standard serum having normal migration activity, for example serum of specially fed pigs, or a selected human serum;

a suitable standard serum having reduced migration activity, for example serum from specially fed pigs, or a selected human serum;

a suitable medium for cultivating cells, for example a modified medium according to Eagle, or a medium according to Dulbecco, or Waymouth's medium;

as well as optionally:

suitable sterile culture dishes made from plastics material;

blades for producing the wound, particularly suitable regarding properties and size, for example corresponding to a halved or full razor blade;

device suitable for holding the blade for making the wound;

device suitable for supporting the culture dishes when the wound is being applied;

a suitable agent for colouring the cell nuclei, for example a 0.15% solution of Leishman's dye in methanol; and a detailed description for carrying out and evaluating the method of diagnosis.

Outfits not containing one or more of the readily obtainable devices and materials designated above as being optionally present are likewise included in the subject matter of the present invention.

What is claimed is:

1. A method of diagnosis of atherosclerosis, which method comprises comparing the migration of endothelial cells or of cells of endothelium-like morphology in vitro, in the presence of serum from the person being examined, with the migration of identical cells in the presence of serum from healthy persons or of other standard sera; and interpreting a reduced migration in the presence of serum of the person being examined as being an indication of the possible existence of atherosclerosis in this person.

2. A method according to claim 1, wherein there is measured the cell migration on monolayer cell cultures in which a part of the cellular layer has been removed.

3. A method according to claim 2, wherein cell migration is measured on a monolayer cell culture in a plastics Petri dish, in which monolayer cell culture there is made a wound about 1 cm wide, which is sharply defined on one side and which extends into the plastics bottom of the dish.

4. A method according to claim 1, wherein cell migration is measured on monolayer cell cultures of pig aorta endothelial cells.

5. A method according to claim 1, wherein cell migration is measured on monolayer cell cultures of Balb/c 3T3-A31 cells as cells having endothelium-like morphology.

6. A method according to claim 4, wherein the medium used for the monolayer cell cultures is Waymouth's medium 752/1.

7. A method according to claim 5, wherein the medium used for the monolayer cell cultures is Dulbecco's medium.

8. A method according to claim 6, wherein the patient's serum to be tested and the standard serum serving as a comparison, respectively, are each added to the medium to give a concentration of 4% to 8%.

9. A method according to claim 7, wherein the patient's serum to be tested and the standard serum serving as a comparison, respectively, are each added to the medium to give a concentration of 4% to 8%.

10. A method according to claim 1, wherein a test duration of less than 30 hours, particularly of 22 hours, is chosen.

11. A method according to claim 3, wherein there is used as a measure of cell migration the number of cells which have migrated, per millimeter of the sharp boundary line, over this line into the initially cell-free wound.

* * * * *